United States Patent [19]

Hach

[11] 4,220,921
[45] Sep. 2, 1980

[54] CONDUCTIVITY PROBE FOR VISCOUS LIQUIDS

[75] Inventor: Clifford C. Hach, Loveland, Colo.

[73] Assignee: Hach Chemical Company, Loveland, Colo.

[21] Appl. No.: 3,600

[22] Filed: Jan. 15, 1979

[51] Int. Cl.² .......................................... G01N 27/06
[52] U.S. Cl. .................................. 324/447; 324/441; 324/65 P; 324/450; 73/425.4 R
[58] Field of Search .............................. 324/446–450, 324/437, 65 P; 73/425.4 R

[56] References Cited

U.S. PATENT DOCUMENTS

| | | | |
|---|---|---|---|
| 1,610,563 | 12/1926 | McIlvaine | 324/439 X |
| 2,553,754 | 5/1951 | Dietert et al. | 324/65 P X |
| 3,000,805 | 9/1961 | Carritt et al. | 324/441 X |

*Primary Examiner*—Alfred E. Smith
*Assistant Examiner*—Charles F. Roberts
*Attorney, Agent, or Firm*—Leydig, Voit, Osann, Mayer & Holt, Ltd.

[57] ABSTRACT

A conductivity probe having a cylindrical body with an annular open-sided groove in which the electrodes are disposed, and a sliding cover wall for the groove biased to a position covering the groove but easily operable with one hand to slide the cover so as to open the groove. Viscous or slurried material can easily enter the groove, be trapped and confined for the conductivity measurement and then readily washed from the groove and surrounding parts for the next operation.

2 Claims, 5 Drawing Figures

CONDUCTIVITY PROBE FOR VISCOUS LIQUIDS

This invention relates generally to liquid conductivity probes and more particularly concerns a conductivity probe well suited for viscous or otherwise not readily flowable liquids.

Pure water is not electrically conductive. However, impurities such as mineral content make water conductive, and it is well known that the level of conductivity provides a measure of the degree of contamination.

The probes for a conductivity meter should place a pair of spaced electrodes in the liquid sample, and should also somehow confine the volume of liquid in the path between the electrodes so as to avoid conduction paths outside of a fixed region and thus avoid errors introduced by the size of the sample being tested or the position of the probe in the sample container. Such containment is usually obtained by having an enclosed region in the probe containing the electrodes to which the liquid under test must flow through a narrow aperture of some kind.

It is difficult if not impossible to use a probe of the above-described type for testing the conductivity of a slurry or a viscous liquid because the sample will not flow easily into the confined path between the electrodes and, if the path is filled, it is difficult to clean out before taking the next sample for test.

Accordingly, it is the primary aim of the invention to provide an easy-to-use conductivity probe that functions well even in viscous or slurried liquids. A related object of the invention is to provide a probe of the above character that can be positioned and manipulated with one hand.

Another object is to provide a probe as described above that is simple in design and economical to manufacture.

Other objects and advantages of the invention will become apparent upon reading the following detailed description and upon reference to the drawings, in which.

Figure 1:
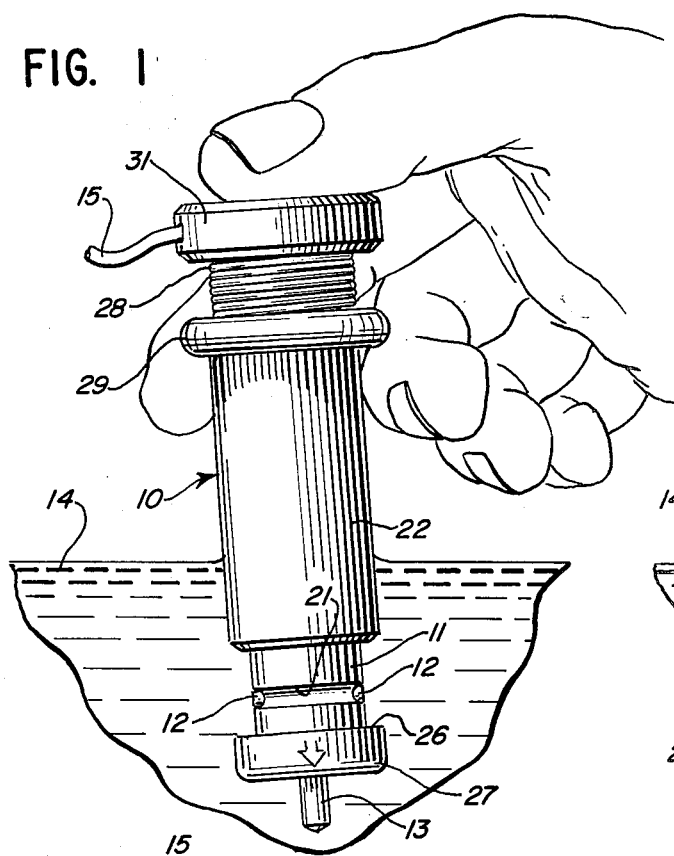
FIG. 1 is a side elevation of a probe embodying the invention being positioned in a liquid sample preparatory to making a reading.

While the invention will be described in connection with a preferred embodiment, it will be understood that I do not intend to limit the invention to that embodiment. On the contrary, I intend to cover all alternatives, modifications and equivalents as may be included within the spirit and scope of the invention as defined by the appended claims.

Turning to the drawings, there is shown a probe 10 embodying the invention and including a body 11 mounting a pair of electrodes 12 and a temperature sensing thermister 13. When inserted in a sample 14 to be tested, a-c. current is conveyed to the electrodes 12 through a pair of leads 15 and the conductivity of the liquid, appropriately compensated by temperature information from the thermister 13 and its leads 15, is displayed as on a meter dial 16 of the conductivity meter with which the probe 10 is used.

Figure 2:
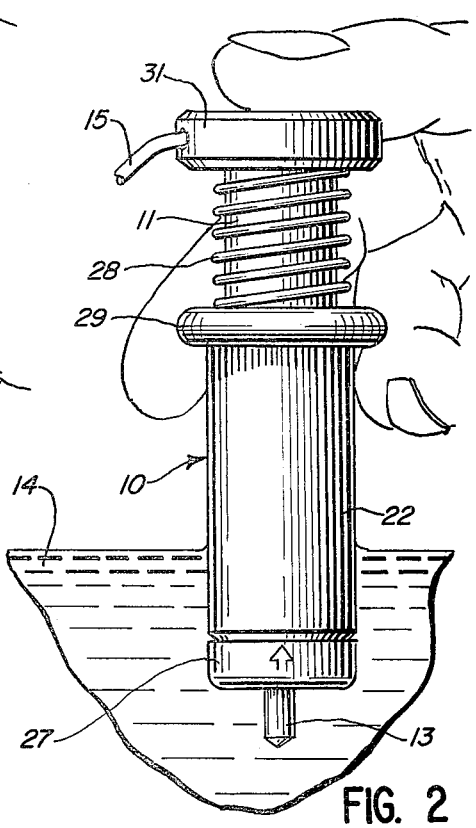
FIG. 2 is similar to FIG. 1 with the parts of the probe in their reading position.
Figure 3:
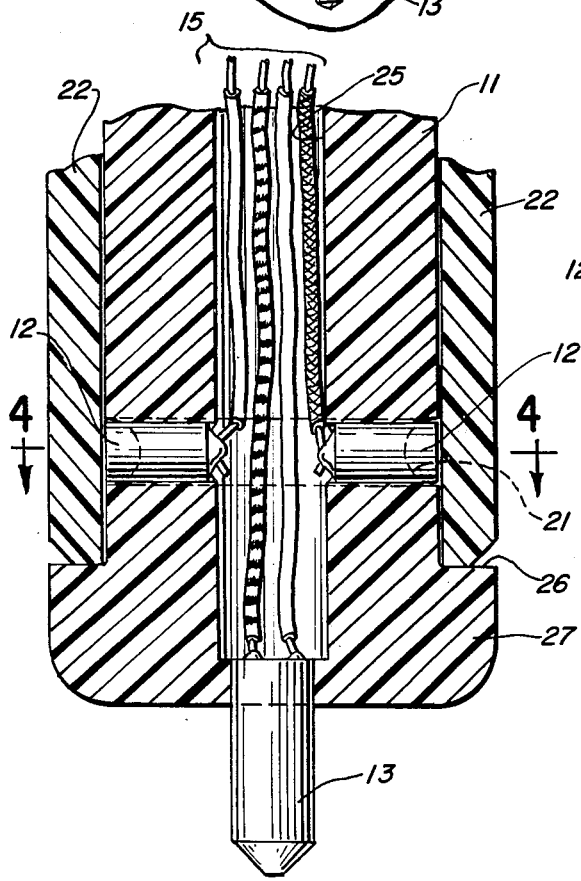
FIG. 3 is an enlarged fragmentary section of the tip of the probe shown in FIG. 1.
Figure 4:
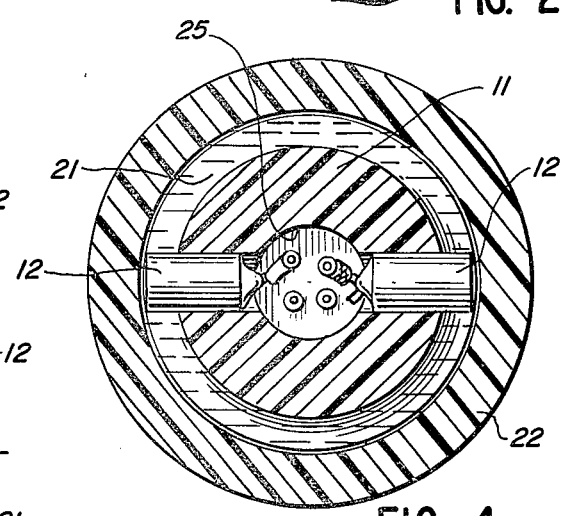
FIG. 4 is a section taken approximately along the line 4—4 in FIG. 3.
Figure 5:
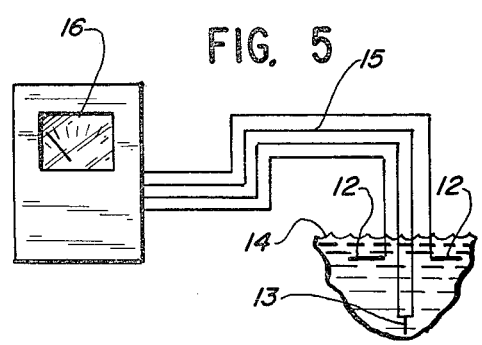
FIG. 5 is a schematic of the wiring of the probe of FIG. 1 to a conductivity meter.

In accordance with the invention, the body 11 is formed with an open-sided groove 21 providing a path connecting the electrodes 12, and a wall 22 is slidably mounted on the body 11 for movement between a rest position closely covering the groove 21 (FIGS. 2 and 3) and an open position completely opening the groove (FIG. 1). Preferably, the body 11 is cylindrical, with a central bore 25 for the leads 15, and the groove 21 is annular with the electrodes 12 being positioned 180° apart. In the illustrated embodiment, the wall 22 is a hollow cylinder closely fitted about the body 11 that, in its rest position, abuts an annular surface 26 on a shoulder 27 at one end of the body 11.

For ease of operation, the cylinder wall 22 is biased toward its rest position by a helical spring 28 surrounding the body 11 between a rim 29 on the wall and an enlarged head 31 on the body 11. This permits simple one-handed operation, much like any biased plunger device, as suggested by FIGS. 1 and 2.

To operate the probe 10, the user inserts the lower end of the probe into the liquid sample 14 and manually, with one hand, presses together the rim 29 and the head 31 so as to completely open the groove 21. The probe is then sloshed around in the event that a viscous liquid or a slurry is being sampled to insure that the sample material fills the groove between the electrodes 12. Pressure on the spring 28 is then relaxed so as to move the wall 22 to its rest position closing the groove and thus confining the liquid sample for the conductivity test. The probe is left in the FIG. 2 position, a-c. current is applied to the electrodes 12, and the reading taken. Upon completing a reading, the spring 28 is again compressed so as to open the groove 21 and expose the lower end of the body 11 whereupon these parts can be easily washed with distilled water to make the probe ready for its next test. Because the groove 21 is open-sided, both entry of the material and cleaning away of material after the test is facilitated.

Those familiar with the art will appreciate that the probe 10 is of very simple design so as to be economically manufactured. Obviously, a non-conductive material such as polyvinylchloride is preferably used for the body 11 and the wall 22.

I claim as my invention:

1. In a conductivity probe, the combination comprising, a non-conductive body, a pair of electrodes mounted on the surface of said body, an open-sided groove providing a path connecting said electrodes, a non-conductive wall slidably mounted on said body for movement between a rest position closely covering said groove and an open position completely opening said groove, means for biasing said wall towards said rest position, and said body and wall having portions permitting one-handed movement of the wall against said bias to said open position.

2. The combination of claim 1 in which said body is cylindrical, said groove is annular and surrounds said body, said electrodes are spaced 180° apart in said groove, and said wall is a hollow cylinder that abuts an annular surface on the body when in said rest position so as to more completely close said groove.

* * * * *